United States Patent

Imaki et al.

Patent Number: 4,904,787
Date of Patent: Feb. 27, 1990

[54] METHOD FOR PRODUCING 2,4-DIHYDROXYQUINOLINE DERIVATIVES

[75] Inventors: Naoshi Imaki, Atsugi; Yuki Takuma, Machida; Mari Oishi, Yokohama, all of Japan

[73] Assignee: Mitsubishi Kasei Corporation, Tokyo, Japan

[21] Appl. No.: 177,045

[22] Filed: Apr. 4, 1988

[51] Int. Cl.$^4$ .................................. C07D 215/220
[52] U.S. Cl. ............................................... 546/155
[58] Field of Search ................................... 546/155

[56] References Cited

FOREIGN PATENT DOCUMENTS 490274 2/1930 Fed. Rep. of Germany.
916103 1/1963 United Kingdom.
1199699 6/1970 United Kingdom.

OTHER PUBLICATIONS

Chemical & Pharmaceutical Bulletin, vol. 29, No. 8, Aug. 1981, pp. 2161–2165; M. Tominaga et al.

Primary Examiner—William R. Dixon, Jr.
Assistant Examiner—Miriam Sohn
Attorney, Agent, or Firm—Oblon, Spivak, McClelland, Maier & Neustadt

[57] ABSTRACT

A method for producing a 2,4-dihydroxyquinoline derivative of the formula:

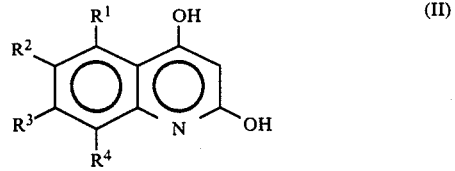

wherein each of $R^1$, $R^2$, $R^3$ and $R^4$ is a hydrogen atom, a lower alkyl group, a lower alkoxy group or a halogen atom, and its tautomer, which comprises cyclizing an aryl malonic acid amide ester derivative of the formula:

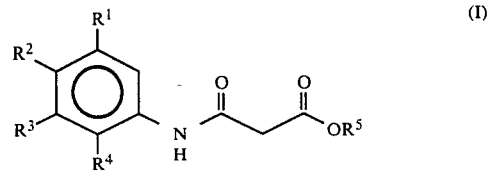

wherein $R^1$, $R^2$, $R^3$ and $R^4$ are as defined above, and $R^5$ is a lower alkyl group, by means of polyphosphoric acid.

4 Claims, No Drawings

METHOD FOR PRODUCING 2,4-DIHYDROXYQUINOLINE DERIVATIVES

The present invention relates to a method for producing 2,4-dihydroxyquinoline derivatives and their tautomers, which are useful as intermediates for the preparation of medicines and agricultural chemicals.

For the production of 2,4-dihydroxyquinoline derivatives, it is known to react an aniline derivative with an excess amount of a malonate for hydrolysis, or to react an aniline derivative with malonic acid. (Michiaki Tominaga et al., Chem. Pharm. Bull., 29(8), 2161–2165 (1981), E. Zieglar and K. Gelfert, Monatsu. Chem., 90,822 (1959), J. L. Bose and R. C. Shah, J. Sci. Ind. Research (India) 19B, 176 (1960), and G. H. Patel and C. M. Mehta, J. Sci. Ind. Research, 19B, 436–438 (1960)).

However, such conventional methods have the following drawbacks. Namely, the method of using a malonate has drawbacks such that is involves a number of process steps although the yield in each step is high, the isolation of intermediats in the respective steps is cumbersome, and the cyclization precursor which is precipitated with an acid from an aqueous solution, contains a substantial amount of water in the crystals and is therefore required to be dried completely. On the other hand, the method for producing a 2,4-dihydroxyquinoline derivative in one step by using malonic acid in the absence of a solvent or in a carboxylic acid solvent such as acetic acid or propionic acid, has drawbacks such that the yield is low, a substantial amount of chlorine gas is produced as a by-product, and the operability of the process is poor although the number of process steps is small.

Under the circumstances, the present inventors have conducted extensive studies to solve such problems of the conventional methods, by paying an attention to the conventional method of using a malonate, wherein the yield in each step is high, and as a result, have found it possible to obtain a 2,4-dihydroxyquinoline derivative in good yield with high selectivity in one step by subjecting the intermediate aryl malonic acid amide ester to a cyclization reaction by means of a certain specific polyphosphoric acid without hydrolyzing it. The present invention has been accomplished on the basis of this discovery.

Namely, it is an object of the present invention to provide a method for readily producing a 2,4-dihydroxyquinoline derivative in good yield and with high selectivity.

The present invention provides a method for producing a 2,4-dihydroxyquinoline derivative of the formula:

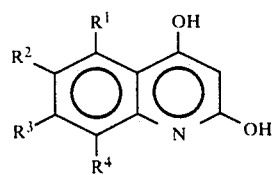

(II)

wherein each of $R^1$, $R^2$, $R^3$ and $R^4$ is a hydrogen atom, a lower alkyl group, a lower alkoxy group or a halogen atom, and its tautomer, which comprises cyclizing an aryl malonic acid amide ester derivative of the formula:

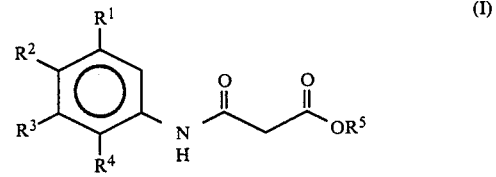

(I)

wherein $R^1$, $R^2$, $R^3$ and $R^4$ are as defined above, and $R^5$ is a lower alkyl group, by means of polyphosphoric acid.

Now, the present invention will be described in detail with reference to the preferred embodiments.

Each of $R^1$ to $R^4$ in the formula I may be a hydrogen atom; an alkyl group having from 1 to 4 carbon atoms such as a methyl group, an ethyl group, a propyl group or a butyl group; an alkoxy group having from 1 to 4 carbon atoms such as a methoxy group, an ethoxy group, a propoxy group or a butoxy group; or a halogen atom such as chlorine or bromine.

$R^5$ is removed by the reaction of the present invention. Therefore, there is no particular restriction as to $R^5$ so long as it does not adversely affect the reaction of the invention. $R^5$ is usually a lower alkyl group such as a methyl group, an ethyl group, a propyl group or a butyl group.

Such an aryl malonic acid amide ester can be prepared by a conventional method and has the above-mentioned substituents. Specifically, it includes a methyl ester, an ethyl ester and a propyl ester of phenyl malonic acid amide, a methyl ester, an ethyl ester, a propyl ester and an isopropyl ester of (2,3-dimethylphenyl) malonic acid amide, a methyl ester, an ethyl ester and a propyl ester of chlorophenyl malonic acid amide, and a methyl ester of methoxyphenyl malonic acid amide.

Each of $R^1$ to $R^4$ is not restricted to the above-mentioned carbon number and may be an alkyl group or an alkoxy group having a higher number of carbon atoms so long as the reaction of the present invention is not adversely affected.

With respect to the polyphosphoric acid to be used in the present invention, it is generally known that a polyphosphoric acid will have a different polymerization degree (n) of a polyphosphoric acid represented by the following formula III by changing the molar ratio of 85% phosphoric acid and phosphorus pentoxide ($P_2O_5$) (F. B. Popp, W. E. McEweu, Chem. Rev., 58,321 (1958)).

(III)

In the present invention, it is possible to use a polyphosphoric acid prepared in a molar ratio of $P_2O_5/H_3PO_4$ within a range of from 0.2 to 2.0. From the viewpoint of the reaction rate and selectivity, it is particularly preferred to employ a polyphosphoric acid prepared in a molar ration of $P_2O_5/H_3PO_4$ within a range of from 0.4 to 0.6.

The polyphosphoric acid is used usually in an amount of from 0.1 to 50 ml, preferably from 0.2 to 20 ml, relative to 1.0 g of the aryl malonic acid amide ester derivative.

Since the polyphosphoric acid serves as a solvent, no other solvent may be employed. However, a solvent which is inert to the reaction of the present invention may be employed as the case requires. For example, a solvent which is not completely missible with the polyphosphoric acid, such as a non-polar solvent such as toluene or xylene, may be employed.

The reaction temperature is usually from 50° to 200° C., preferably from 100° to 150° C., since the lower the temperature, the higher the selectivity.

The 2,4-dihydroxyquinoline derivative obtained by the present invention is represented by the formula II. However, the compound of the present invention can take the form of its tautomer represented by the following formula II'.

Thus, the compound of the formula II' is also within the scope of the present invention.

Now, the present invention will be described in further detail with reference to Examples. However, it should be understood that the present invention is by no means restricted by such specific Examples.

In the Examples, the analytical condition for the liquid chromatography (LC) are as follows:
Column: Nucleosil-5-CN
Mobile phase: 0.05 mol $KH_2PO_4/CH_3CN = 85$ vol%/15 vol%
Temperature: 45° C.
Flow rate: 1.0 ml/min.
Detection method: UV-230 nm

EXAMPLE 1

50 g of $P_2O_5$ was added to 50 ml of 85% $H_3PO_4$, and the mixture was stirred at 100° C. for two hours to obtain polyphosphoric acid. (Molar ratio of $P_2O_5/H_3PO_4$: 0.48)

1 ml of the above polyphosphoric acid was added to 0.1 g of a methyl ester of (2,3-dimethylphenyl) malonic acid amide, and the mixture was reacted at 130° C. for two hours. After completion of the reaction, the reaction solution was poured into water, and subjected to liquid chromatography analysis (LC analysis). The starting material i.e. the dimethyl ester of (2,3-dimethylphenyl) malonic acid amide was not observed (conversion: 100%), and 65.1 mg (yield: 75%) of 4-hydroxy-7,8-dimethyl-2-quinolone as the desired product, 0.1 mg (yield: 1%) of mono(2,3-dimethylphenyl) malonic acid amide as an intermediate and 7.7 mg (yield: 14%) of 2,3-xylidine as a by-product were obtained. The results are shown in Table 1.

EXAMPLE 2

25 g of $P_2O_5$ was added to 20 ml of 85% $H_3PO_4$, and the mixture was stirred at 100° C. for two hours to obtain polyphosphoric acid. (Molar ratio of $P_2O_5/H_3PO_4$: 0.6)

1 ml of the above polyphosphoric acid was added to 0.1 g of a methyl ester of (2,3-dimethylphenyl) malonic acid amide, and the mixture was reacted at 130° C. for two hours. After completion of the reaction, the reaction solution was poured into water and subjected to LC analysis.

The starting material i.e. the dimethyl ester of (2,3-dimethylphenyl) malonic acid amide was not observed (conversion: 100%), 58.8 mg (yield: 67%) of 4-hydroxy-7,8-dimethyl-2-quinolone as the desired product, 7.1 mg (yield: 7%) of mono(2,3-dimethylphenyl) malonic acid amide as an intermediate and 6.9 mg (yield: 12%) of 2,3-xylidine as a by-product were obtained. The results are shown in Table 1.

EXAMPLE 3

61.2 g of $P_2O_5$ was added to 39 ml of 85% $H_3PO_4$, and the mixture was stirred at 100° C. for two hours to obtain polyphosphoric acid. (Molar ratio of $P_2O_5/H_3PO_4$: 0.76)

1 ml of the above polyphosphoric acid was added to 0.1 g of a methyl ester of (2,3-dimethylphenyl malonic acid amide, and the mixture was stirred at 130° C. for two hours. After completion of the reaction, the reaction solution was poured into water and subjected to LC analysis.

The starting material i.e. the dimethyl ester of (2,3-dimethylphenyl) malonic acid amide was not observed (conversion: 100%), and 46.8 mg (yield: 54%) of 4-hydroxy-7,8-dimethyl-2-quinolone as the desired product, 18.0 mg (yield: 19%) of mono(2,3-dimethylphenyl) malonic acid amide as an intermediate and 4.6 mg (yield: 8%) of 2,3-xylidine as a by-product were obtained. The results are shown in Table 1.

EXAMPLE 4

25 g of $P_2O_5$ was added to 12 ml of 85% $H_3PO_4$, and the mixture was stirred at 100° C. for two hours to obtain polyphosphoric acid. (Molar ratio of $P_2O_5/H_3PO_4$: 1.0)

1 ml of the above polyphosphoric acid was added to 0.1 g of a methyl ester of (2,3-dimethylphenyl) malonic acid amide, and the mixture was reacted at 130° C. for two hours. After completion of the reaction, the reaction solution was poured into water and subjected to LC analysis.

The starting material i.e. the dimethyl ester of (2,3-dimethylphenyl) malonic acid amide was not observed (conversion: 100%, and 38.2 g (yield: 44%) of 4-hydroxy-7,8-dimethyl-2-quinolone as the desired product, 21.8 mg (yield: 23%) of mono(2,3-dimethylphenyl) malonic acid amide as an intermediate and 1.7 mg (yield: 3%) of 2,3-xylidine as a by-product were obtained. The results are shown in Table 1.

EXAMPLE 5

1 ml of the polyphosphoric acid (molar ratio of $P_2O_5/H_3PO_4$: 0.48) as used in Example 1 was added to 0.1 g of an ethyl ester of (2,3-dimethylphenyl) malonic acid amide, and the mixture was reacted at 130° C. for two hours. After completion of the reaction, the reaction solution was poured into water and subjected to LC analysis. The starting material i.e. the ethyl ester of (2,3-dimethylphenyl) malonic acid amide was not observed (conversion: 100%), and 70.5 mg (yield: 86%) of 4-hydroxy-7,8-dimethyl-2-quinolone as the desired product, 3.3 mg (yield: 4%) of mono(2,3-dimethylphenyl) malonic acid amide as an intermediate and 5.8 mg (yield: 11%) of 2,3-xylidine as a by-product were obtained. The results are shown in Table 1.

EXAMPLE 6

1 ml of the polyphosphoric acid (molar ratio of $P_2O_5/H_3PO_4$: 0.48) as used in Example 1 was added to 0.1 g of an isopropyl ester of (2,3-dimethylphenyl) malonic acid amide, and the mixture was reacted at 130° C. for two hours. After completion of the reaction, the reaction solution was poured into water, and subjected to LC analysis. The starting material i.e. the isopropyl ester of (2,3-dimethylphenyl) malonic acid amide was not observed (conversion: 100%), and 19.6 mg (yield: 26%) of 4-hydroxy-7,8-dimethyl-2-quinolone as the desired product, 0.5 mg (yield: 0.6%) of mono(2,3-dimethylphenyl) malonic acid amide as an intermediate and 0.6 g (yield: 1%) of 2,3-xylidine as a by-product were obtained. The results are shown in Table 1.

EXAMPLE 7

5 ml of the polyphosphoric acid (molar ratio of $P_2O_5/H_3PO_4$: 0.48) as used in Example 1 was added to 0.1 g of a methyl ester of (2,3-dimethylphenyl) malonic acid amide and the mixture was reacted at 130° C. for two hours. After completion of the reaction, the reaction solution was poured into water and subjected to LC analysis.

The starting material i.e. the methyl ester of (2,3-dimethylphenyl) malonic acid amide was not observed (conversion: 100%), and 68.9 mg (yield: 79%) of 4-hydroxy-7,8-dimethyl-2-quinolone as the desired product, 0.1 mg (yield: 0.1%) of mono(2,3-dimethylphenyl) malonic acid amide as an intermediate and 6.6 mg (yield: 12%) of 2,3-xylidine as a by-product were obtained. The results are shown in Table 1.

EXAMPLE 8

0.5 ml of the phosphoric acid (molar ratio of $P_2O_5/H_3PO_4$: 0.48) as used in Example 1 was added to 0.1 g of an ethyl ester of (2,3-dimethylphenyl) malonic acid amide, and the mixture was reacted at 130° C. for two hours. After completion of the reaction, the reaction solution was poured into water and subjected to LC analysis.

The starting material i.e. the ethyl ester of (2,3-dimethylphenyl) malonic acid amide was 5.1 mg (conversion: 95%), and 63.7 mg (yield: 79%) of 4-hydroxy-7,8-dimethyl-2-quinolone as the desired product, 3.4 mg (yield: 4%) of mono(2,3-dimethylphenyl) malonic acid amide as an intermediate and 3.3 mg (yield: 6%) of 2,3-xylidine as a by-product were obtained. The results are shown in Table 1.

TABLE 1

| | Aryl malonic acid amide ester derivative | Reaction conditions | | | Conversion of aryl malonic acid amide ester (%) | Yield of 2,4-dihydroxy-quinoline derivative (%) | Yield of 2,3-xylidine (%) | Yield of mono-(2,3-dimethylphenyl) malonic acid amide (%) |
|---|---|---|---|---|---|---|---|---|
| | | Temp. (°C.) | Time (hr) | Molar ratio of $P_2O_5/H_3PO_4$ | | | | |
| Example 1 | Methyl ether of (2,3-dimethyl-phenyl) malonic acid amide | 130 | 2 | 0.48 | 100 | 75 | 14 | 1 |
| Example 2 | Methyl ether of (2,3-dimethyl-phenyl) malonic acid amide | " | " | 0.60 | 100 | 67 | 12 | 7 |
| Example 3 | Methyl ether of (2,3-dimethyl-phenyl) malonic acid amide | " | " | 0.76 | 100 | 54 | 8 | 19 |
| Example 4 | Methyl ether of (2,3-dimethyl-phenyl) malonic acid amide | " | " | 1.0 | 100 | 44 | 3 | 23 |
| Example 5 | Ethyl ether of (2,3-dimethyl-phenyl) malonic acid amide | " | " | 0.48 | 100 | 86 | 11 | 4 |
| Example 6 | Isopropyl ester of (2,3-dimethyl-phenyl) malonic acid amide | 130 | 2 | 0.48 | 100 | 26 | 1 | 0.6 |
| Example 7 | Methyl ester of (2,3-dimethyl-phenyl) malonic acid amide | " | " | " | 100 | 79 | 12 | 0.1 |
| Example 8 | Ethyl ester of (2,3-dimethyl-phenyl) malonic acid amide | " | " | " | 95 | 79 | 6 | 4 |

According to the present invention, the cyclization reaction can be conducted in good yield and with high selectivity in one step reaction, and the 2,4-dihydroxyquinoline derivative as the desired product can readily be prepared. In particular, 7,8-dimethyl-2,4-dihydroxyquinoline produced by the method of the present invention is particularly useful as an intermediate for the preparation of a compound useful as a treating agent of allergic asthema (Japanese Unexamined Patent Publication No. 109000/1977).

REFERENCE EXAMPLE 1

10 g of 4-hydroxy-7,8-dimethyl-2-quinolone was added to 60 cc of ethylene dichloride, and 14 g of aluminum chloride was added thereto under stirring at room temperature. The reaction solution was first slurried by the formation of a complex and then became a uniform solution. Then, a solution of a mixture of 5.3 cc of acetyl chloride and 16 cc of ethylene dichloride was dropwise added thereto at room temperature, and the acetylation reaction was conducted at 50° C. for 3 hours. The reaction solution was cooled to room temperature, and 50 cc of water was carefully added for hydrolysis. Then, 5 cc of propionic acid was added thereto, and ethylene dichloride was distilled off together with water under heating, and the mixture was aged at 100° C. for 3 hours under stirring. The slurry was cooled at room temperature and subjected to filtration. The obtained crystals were dried to obtain 11.5 g of 3-acetyl-4-hydroxy-7,8-dimethyl-2-quinolone. Yield was 94%, and the purity was 98% (as analyzed by liquid chromatography).

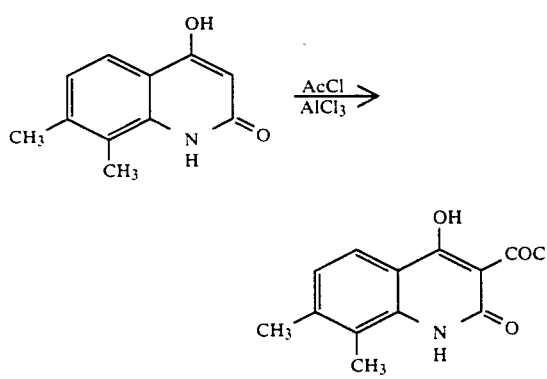

REFERENCE EXAMPLE 2

4.54 g of 63% sodium hydride was added to 66 cc of toluene, and while stirring the mixture at room temperature, 33 cc of isoamyl alcohol was dropwise added thereto. The mixture was further stirred at 50° C. for one hour to obtain sodium isoamyl alcolate. Then, 10 g of 3-acetyl-4-hydroxy-7,8-dimethyl-2-quinolone was added in its solid state thereto, and 20 g of diisoamyl oxalate was dropwise added thereto, whereupon the condensation reaction was conducted at 50° C. for 3 hours. The reaction solution was initially a slurry, but then changed into a reddish brown uniform solution. The reaction solution was cooled to room temperature, and then acidified with the mixture of 7.38 g of concentrated sulfonic acid, 47 cc of isoamyl alcohol and 14 cc of toluene. Then, the cyclization reaction was conducted at 80° C. for two hours while removing formed water. The reaction solution was initially a yellow slurry but turned into a substantially uniform solution at the completion of the reaction. Then, toluene was distilled off under reduced pressure at 40° C., and 130 cc of n-heptane was added. The mixture was subjected to precipitation at room temperature for one hour. The slurry thereby obtained was neutralized with an aqueous solution of 0.5 N sodium bicarbonate. The crystals were collected by filtration and washed twice with 50 cc of water and dried under reduced pressure to obtain 13.52 g of isoamyl-5,6-dihydro-7,8-dimethyl-4,5-dioxo-4H-pyrano[3,2-C]quinolone-2-carboxylate (yield: 88% based on 3-acetyl-4-hydroxy-7,8-dimethyl-2-quinolone) with a purity of 99% (as measured by liquid chromatography).

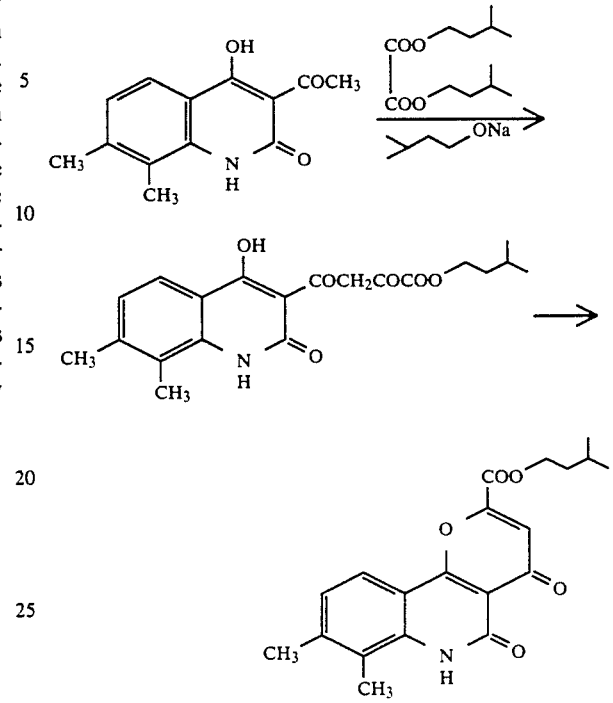

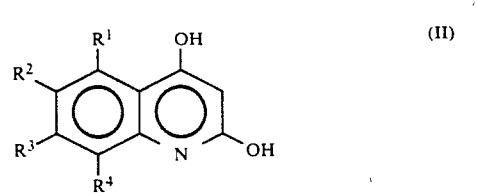

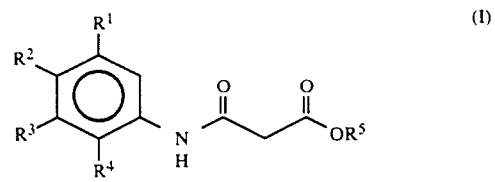

I claim:

1. A method for producing a 2,4-dihydroxyquinoline compound of the formula:

(II)

wherein each of $R^1$, $R^2$, $R^3$ and $R^4$ is a hydrogen atom, a lower alkyl group, a lower alkoxy group or a halogen atom, and its tautomer, which comprises cyclizing an aryl malonic acid amide ester compound of the formula:

(I)

wherein $R^1$, $R^2$, $R^3$ and $R^4$ are as defined above, and $R^5$ is a lower alkyl group, by means of polyphosphoric acid at a temperature of from 50° C. to 200° C., wherein said polyphosphoric acid is prepared in a molar ratio of $P_2O_5/H_3PO_4$ within a range of from 0.4 to 0.6.

2. The method of claim 1, wherein said cyclizing is carried out in a solvent which is selected from the group consisting of toluene and xylene.

3. The method of claim 1, wherein said temperature is from 100° to 150° C.

4. The method of claim 4, wherein said polyphosphoric acid is present in an amount of from 0.1 to 50 ml relative to 1.0 g of said aryl malonic acid amide ester compound.

* * * * *